Sept. 11, 1951 F. W. ANDERSON Plant Pat. 1,035
NECTARINE TREE
Filed Sept. 9, 1950
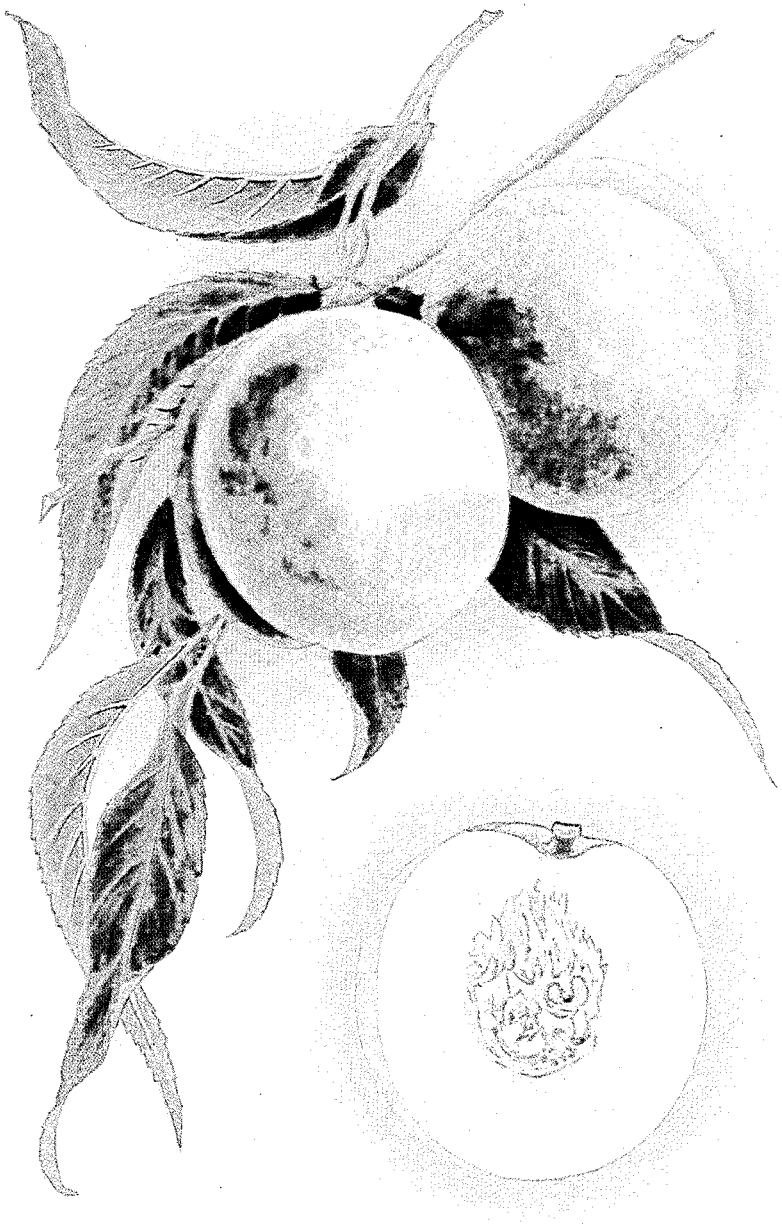
WITNESS
Addison F. Avery
INVENTOR
F. W. ANDERSON
Webster & Webster
ATTYS Patented Sept. 11, 1951 Plant Pat. 1,035

UNITED STATES PATENT OFFICE 1,035

NECTARINE TREE

Frederic W. Anderson, Merced, Calif.

Application September 9, 1950, Serial No. 183,975

1 Claim. (Cl. 47—62)

This invention is directed to a new and distinct variety of nectarine tree having yellow fleshed clingstone fruit.

The variety is the result of a long-time selective breeding program which I have carried forward to obtain more commercially desirable nectarines.

The herein described variety of nectarine tree bears close resemblance to the Le Grand variety (United States Plant Patent No. 549), but the present variety is distinctive in comparison thereto in that it has a ripening period which is approximately three weeks later.

This new and distinct variety of nectarine tree was originated by me on my ranch near Merced, county of Merced, State of California, in the following manner:

Several thousand open-pollenated seeds of the Le Grand nectarine were planted in 1942, and subsequently came into bearing in a nursery row. Among these seedlings there appeared the instant variety, and which was recognized by me as distinctive by reason of its ripening period about three weeks later than the parent Le Grand variety.

The present variety was thus originated as an open-pollenated seedling of the Le Grand variety, and subsequently was top-worked on mature orchard trees at my ranch, located as aforesaid.

These top-worked trees have come into bearing, and such asexual reproductions are found to retain in full the novel characteristics of the parent tree of the new variety.

The ripening period, during the same season of comparison, was the third week of August for the new variety, as compared to the last week in July for the Le Grand variety.

The ripening of the herein claimed variety may be further compared as follows:

The present leading varieties of nectarines in California, all of which are grown and shipped commercially by me, are—in the order of their ripening—

John Rivers
Gower
Quetta
Stanwick and the yellow-fleshed varieties:

Bim (United States Plant Patent No. 575)
Kim (United States Plant Patent No. 173), and
Le Grand (United States Plant Patent No. 549).

As compared to the well-known Elberta peach, the above seven varieties ripen as follows:

John Rivers—six weeks (approximately forty-three days before Elberta).

Gower—two weeks (approximately thirteen days before Elberta).

Bim—one and one-half weeks (approximately ten days before Elberta).

Kim—one and one-half weeks (approximately nine days before Elberta).

Le Grand—one-half week (approximately four days before Elberta).

Quetta—one-half week (approximately four days before Elberta).

Stanwick—two weeks (approximately thirteen days after Elberta).

The Le Grand nectarine, which the present variety most closely resembles—as aforesaid—ripens more nearly with the J. H. Hale peach; viz., picking begins three or four days before the Elberta peach, and extends from four to eight days after the latter.

In relative comparison to the above, the present novel variety of nectarine ripens approximately three weeks after the Elberta peach, or slightly later than the Stanwick nectarine.

As compared with the Stanwick nectarine, which has long been a standard nectarine variety, the present variety has yellow instead of white flesh; has firm instead of soft texture; and averages at least one-third larger in fruit size, being very similar to the Le Grand in all fruit and tree characteristics, except ripening some three weeks later than the latter.

In the drawings:

Fig. 1 is a perspective view of the fruit on a twig and in association with a representation of the leaves of the variety.

Fig. 2 is a sectional view of the fruit with the stone exposed.

Referring now specifically to the new and distinct variety of nectarine tree, the following is a detailed description thereof in outline; all color plate identifications being by reference to Maerz and Paul Dictionary of Color:

Tree: Large; vigorous; spreading; productive; regular bearer.

Trunk: Stocky.

Branches: Stocky. Above medium in size.

*Lenticels:* Medium in number and size.

Leaves: Average length, 6 to 7 inches; average width, 1¾ to 2 inches. Large size; smooth. Color—medium green (top side 22-L-7; under side 22-K-4).

*Margin.*—Crenate.

*Petiole.*—Medium in length and thickness.

*Glands.*—Average four in number. Alternate; medium size; reniform. Usually located two on the petiole and two or more on the margins of the blade. Stipules—none.

Flower buds: Medium size; plump.

Flowers: Large size; showy. Color—pink. Blossom period—about with the Elberta peach.

Fruit:

*Size.*—Size extremely large for a nectarine, being larger in size than any commercially grown nectarine except the Le Grand variety. Well grown specimens average three inches in ring diameter and slightly more from stem to apex, being somewhat variable in shape.

*Shape.*—Globose to oblong.

*Suture.*—Shallow, with a marked depression beyond the pistil point.

*Ventral surface.*—Rounded, with lips equal.

*Cavity.*—Rounded, approximately ⅜ inch in diameter and ¾ inch in breadth, usually marked with red lines.

*Base.*—Rounded.

*Apex.*—Depressed, with pistil point almost lacking.

*Stem.*—Stout, and adheres strongly to stone (like the J. H. Hale).

*Skin.*—Above medium in thickness and toughness; tenacious to the flesh. Color—Yellow (11–L–8), but usually completely overspread with Red (55–L–1), shading into 56–L–12. Pubescence—none.

*Flesh.*—Color—Yellow; lightest area (9–J–5), shading through (11–K–5) to (11–L–6), streaked with Red (55–L–12) next to stone. Surface of pit cavity—red with yellow fibers. Amygdalin—moderate. Juice—abundant. Fibers—abundant. Texture of flesh—very firm. Ripens—evenly. Flavor—delicate and somewhat acid. Aroma—distinct. Eating quality—very good to best.

*Stone.*—Cling. Fibers—long. Size—large, averaging 1⅜ inches in length, 1¼ inches in breadth, and ⅝ inch in thickness. Form — oval. Base — oblique. Hilum — broad and oval. Apex—rounded. Sides—equal. Surface—irregularly furrowed and pitted throughout. Ventral side—thick. Dorsal edge—full, with deep grooves. Ridges—continuous. Color—Reddish (55–L–12). Some tendency toward splitting.

*Resistance to insects and diseases.*—Medium.

*Keeping and shipping quality.*—Very good, having firm flesh with uniform ripening comparable to the J. H. Hale peach or Le Grand nectarine.

The tree and its fruit herein described may vary in slight detail due to climatic and soil conditions under which the variety may be grown.

Having thus described my invention, I claim:

A new and distinct variety of nectarine tree, as shown and described, characterized by its close physical resemblance to the Le Grand nectarine, including large clingstone fruit which is yellow, blushed red exteriorly and with firm yellow flesh, but having a ripening period approximately three weeks later than said Le Grand nectarine; such ripening period being about the end of the Stanwick nectarine harvest.

FREDERIC W. ANDERSON.

No references cited.